United States Patent [19]

Wick et al.

[11] 4,430,334
[45] Feb. 7, 1984

[54] PHENETHANOLAMINE DERIVATIVES FOR USE AGAINST CEREBROVASCULAR DISEASE

[75] Inventors: Alexander E. Wick, Saint Nom La Breteche; Jonathan R. Frost, Cachan, both of France

[73] Assignee: Synthelabo, Paris, France

[21] Appl. No.: 368,002

[22] Filed: Apr. 13, 1982

[30] Foreign Application Priority Data

Apr. 14, 1981 [FR] France ................. 81 07445

[51] Int. Cl.³ ............... A61K 31/445; C07D 211/14
[52] U.S. Cl. ................... 424/267; 546/237; 546/240
[58] Field of Search ................ 546/240; 424/267

[56] References Cited

PUBLICATIONS

*Chemical Abstracts*, 96:34826w (1982)[Japan Kokai No. 81,128,740, Greian, 10/8/81].
*Chemical Abstracts*, 94:103169g (1981)[Belg. Pat. No. 878,876, 3/1980].
*Chemical Abstracts*, 95:187089n (1981)[Japan Kokai No. 81779,666, 6/30/81].
*Chemical Abstracts*, 76:59395e (1972)[Carron, C., et al., Arzneim.-Forsch. 1971, 21(12), 1992–1998].
*Chemical Abstracts*, 95:161806u (1981)[Young, A., et al., J. Cereb. Blood Flow Metab. 1981, 1(1), 117–128].

*Primary Examiner*—Richard A. Schwartz
*Attorney, Agent, or Firm*—Wegner & Bretschneider

[57] ABSTRACT

Phenethanolamine derivatives in the (+)-erythro form of the formula:

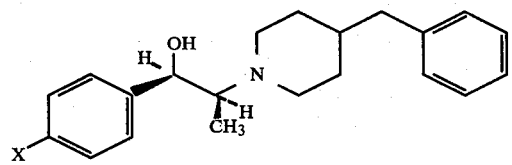

wherein X represents a halogen atom, are new compounds useful in therapy.

8 Claims, No Drawings

PHENETHANOLAMINE DERIVATIVES FOR USE AGAINST CEREBROVASCULAR DISEASE

This invention relates to new therapeutically useful phenethanolamine derivatives, to a process for their preparation and pharmaceutical compositions containing them.

The phenethanolamine derivatives of the present invention are those compounds in the (±)-erythro form of the formula:

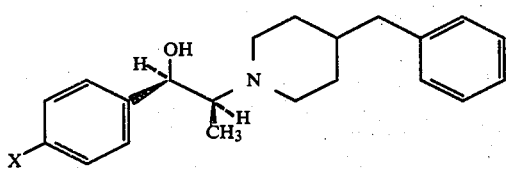

wherein X represents a halogen atom, and pharmaceutically acceptable acid addition salts thereof, e.g. the hydrochlorides.

According to a feature of the invention the phenethanolamine derivative of formula (I) in (±)-erythro form are prepared by reacting a 4-halogenopropiophenone of the formula:

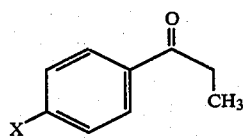

(wherein X is as hereinbefore defined) with bromine in an organic solvent such as chloroform, reacting the resulting brominated compound of the formula:

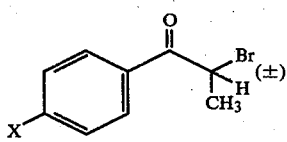

(wherein X is as hereinbefore defined) with 4-benzylpiperidine of the formula:

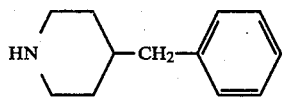

in an organic solvent such as ethanol, in the presence of a base such as sodium carbonate, and reducing the carbonyl radical in the resulting compound of the formula:

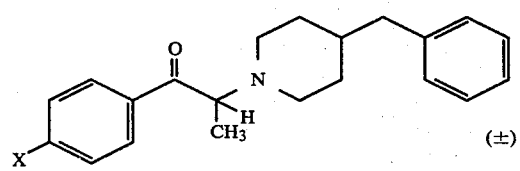

(wherein X is as hereinbefore defined) to >CH—OH, for example using potassium borohydride in an acid medium such as acetic acid.

Pharmaceutically acceptable acid addition salts of the phenethanolamine derivatives of formula (I) can be obtained by methods known per se, for example by reacting the phenethanolamine base with an acid, the anion of which is relatively innocuous to the animal organism in therapeutic doses of the salts, e.g. hydrochloric, methanesulphonic, fumaric or maleic acid.

The following Example illustrates the preparation of compounds of this invention.

The analyses and the IR and NMR spectra confirm the structure of the compounds.

EXAMPLE 2-(4-Benzylpiperidino)-1-(4-chlorophenyl)-propan-1-ol and its hydrochloride (in the (±)-erythro form)

1. 2-Bromo-4'-chloropropiophenone.

A solution of 15.9 g (0.1 mol) of bromine in 20 ml of CHCl₃ is slowly added dropwise to a solution of 16.8 g (0.1 mol) of 4-chloropropiophenone in 100 ml of CHCl₃, in the presence of AlCl₃. The mixture is stirred overnight. After filtration through a glass plug and after evaporation of the solvent, the crystalline residue is washed with petroleum ether. The compound melts at 75° C.

2. 4'-Chloro-2-(4-benzylpiperidino)-propiophenone.

14.7 g (0.084 mol) of 4-benzylpiperidine and then 10 g (0.084 mol) of sodium carbonate are added to a solution of 20.8 g (0.084 mol) of the compound obtained as described above in 100 ml of ethanol. The mixture is heated at the reflux temperature for 2 hours. It is then cooled with the aid of an ice-bath. The reaction mixture is poured onto 500 ml of ice, and 250 ml of toluene are added. The mixture is stirred vigorously and left to separate out. The organic solution is washed and evaporated. The compound crystallises. After recrystallisation from 100 ml of ethanol, it melts at 92° C.

3. 2-(4-Benzylpiperidino)-1-(4-chlorophenyl)propan-1-ol and its hydrochloride (in the (±)-erythro form).

20 ml of acetic acid are added to a solution of 4.3 g (0.0125 mol) of the compound obtained as described in experiment 2 above in 40 ml of ethanol. The reaction mixture is immersed in an ice-bath, and 3 g of KBH₄ are added gradually, whilst stirring. The mixture is stirred for 1 hour at ambient temperature. 100 ml of a mixture of water and ice and 100 ml of CH₂Cl₂ are added. The mixture is rendered alkaline with 15 ml of concentrated ammonia solution, stirred and the organic phase is then decanted. The aqueous phase is extracted with 60 ml of CH₂Cl₂. The organic phases are washed and evaporated. The crystalline residue is dried by azeotropic distillation with toluene. The residue is taken up in 50 ml of ethanol. The suspension is heated to the reflux temperature and 15 ml of ethanol saturated with hydrogen chloride are added. The reaction mixture is cooled in an ice-bath and filtered. The hydrochloride of the compound obtained is recrystallised from 60 ml of ethanol; its melting point is 240°–246° C.

The following Table by reference to formula (I) shows the compounds prepared by way of Examples.

TABLE

| Compound | X | Melting point (°C.) |
|---|---|---|
| 1 | Cl | 240–246 |
| 2 | F | 239–240 |

TABLE-continued

| Compound | X | Melting point (°C.) |
| --- | --- | --- |
| 3 | Br | 250 (decomposition) |

The phenethanolamine compounds of the invention were subjected to pharmacological experiments.

The toxicity (50% lethal dose, LD 50) of the compounds was determined on mice of the CD1 strain by a graphical method.

The LD 50 is equal to or less than 1000 mg/kg animal body weight, administered intraperitoneally, and it is more than 1000 mg/kg animal body weight, administered orally.

The compounds of the invention were subjected to the complete cerebral ischaemia test. The ischaemia is due to a cardiac arrest induced by a rapid intravenous injection of $MgCl_2$. In this test, the "survival time" is measured, that is to say the interval between the time of injection of $MgCl_2$ and the last observable inspiratory movement of each mouse. This last movement is considered to be the final indication of a function of the central nervous system.

The respiratory arrest appears approximately 19 seconds after the injection of $MgCl_2$.

Male mice (Charles River CD1) are studied in groups of 10. The mice are supplied with food and drink ad libitum before the experiments. The survival time is measured 10 minutes after the intraperitoneal administration of the compounds of the invention.

The results are given in the form of the difference between the survival time measured on a group of 10 mice which have received the compound in a liquid vehicle, and the survival time measured on a group of 10 mice which have received the liquid vehicle.

The ratios of the modifications in the survival time to the dose of compound are recorded graphically on a semilogarithmic curve.

This curve makes it possible to calculate the 3-second effective dose ($ED_{3''}$), that is to say the dose (in mg/kg animal body weight) which produces an increase of 3 seconds in the survival time, relative to the control group of 10 untreated mice.

An increase of 3 seconds in survival time is both statistically significant and reproducible.

The $ED_{3''}$ of the compounds of the invention varies from 25 to 30 mg/kg animal body weight, administered intraperitoneally.

The pharmacological study of the phenethanolamine compounds of the invention shows that they possess an antianoxic activity and that they can be used in therapy for the treatment of vigilance disorders, in particular for combating the behavioural disorders which can be attributed to cerebral vascular damage and to the cerebral sclerosis encountered in geriatrics, and also for the treatment of the absences due to cranial traumatisms, for the treatment of metabolic encephalopathies and for the treatment of depressive states.

The invention consequently includes all pharmaceutical compositions containing, as an active ingredient, a phenethanolamine derivative of formula (I) (in (±)-erythro form), or a pharmaceutically acceptable acid addition salt thereof, in association with any excipient which is suitable for their administration, in particular their oral or parenteral administration.

The methods of administration can be oral and parenteral. The daily dosage can range from 1 to 100 mg, administered parenterally, and from 5 to 500 mg, administered orally.

We claim:

1. A phenethanolamine derivative in the (±)-erythro form of the formula:

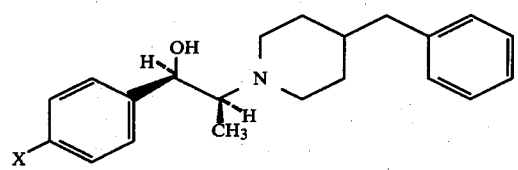

wherein X represents a halogen atom, or a pharmaceutically acceptable acid addition salt thereof.

2. The phenethanolamine derivative according to claim 1 wherein X is chlorine.

3. The phenethanolamine derivative according to claim 1 wherein X is fluorine.

4. The phenethanolamine derivative according to claim 1 wherein X is bromine.

5. A pharmaceutical composition for the treatment of cerebrovascular disease which comprises an effective dose for such treatment of a phenethanolamine derivative in the (±)-erythro form of the formula:

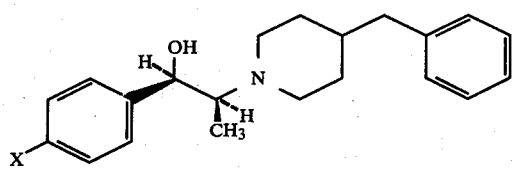

wherein X represents a halogen atom, or a pharmaceutically acceptable acid addition salt thereof, in association with a pharmaceutical excipient suitable for oral or parenteral administration.

6. A method for the treatment of depressive disorders, comprising administering to a patient a therapeutically effective amount of the phenethanolamine derivative of claim 1 or a pharmaceutically acceptable acid addition salt thereof.

7. A method for the treatment of cerebrovascular disease, which comprises administering to a patient a therapeutically effective amount of the phenethanolamine derivative of claim 1 or a pharmaceutically acceptable acid addition salt thereof.

8. A method for the treatment of metabolic encephalopathies which comprises administering to a patient a therapeutically effective amount of the phenethanolamine derivative of claim 1 or a pharmaceutically acceptable acid addition salt thereof.

* * * * *